US00PP34517P2

(12) United States Plant Patent
Danziger

(10) Patent No.: US PP34,517 P2
(45) Date of Patent: Aug. 23, 2022

(54) ***IBERIS* PLANT NAMED 'DIBFRFLAL'**

(50) Latin Name: *Iberis sempervirens*
Varietal Denomination: DIBFRFLAL

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/472,965

(22) Filed: Sep. 13, 2021

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Cassandra Bright

(57) ABSTRACT

A new and distinct variety of *Iberis* plant named 'DIBFRFLAL' is disclosed, characterized by a controlled and mounded plant habit. Plants produce abundant light lavender colored flowers in the first year. Vernalization is not required for flowering. The new variety is an *Iberis*, useful for ornamental horticulture purposes.

2 Drawing Sheets

Figure 1:
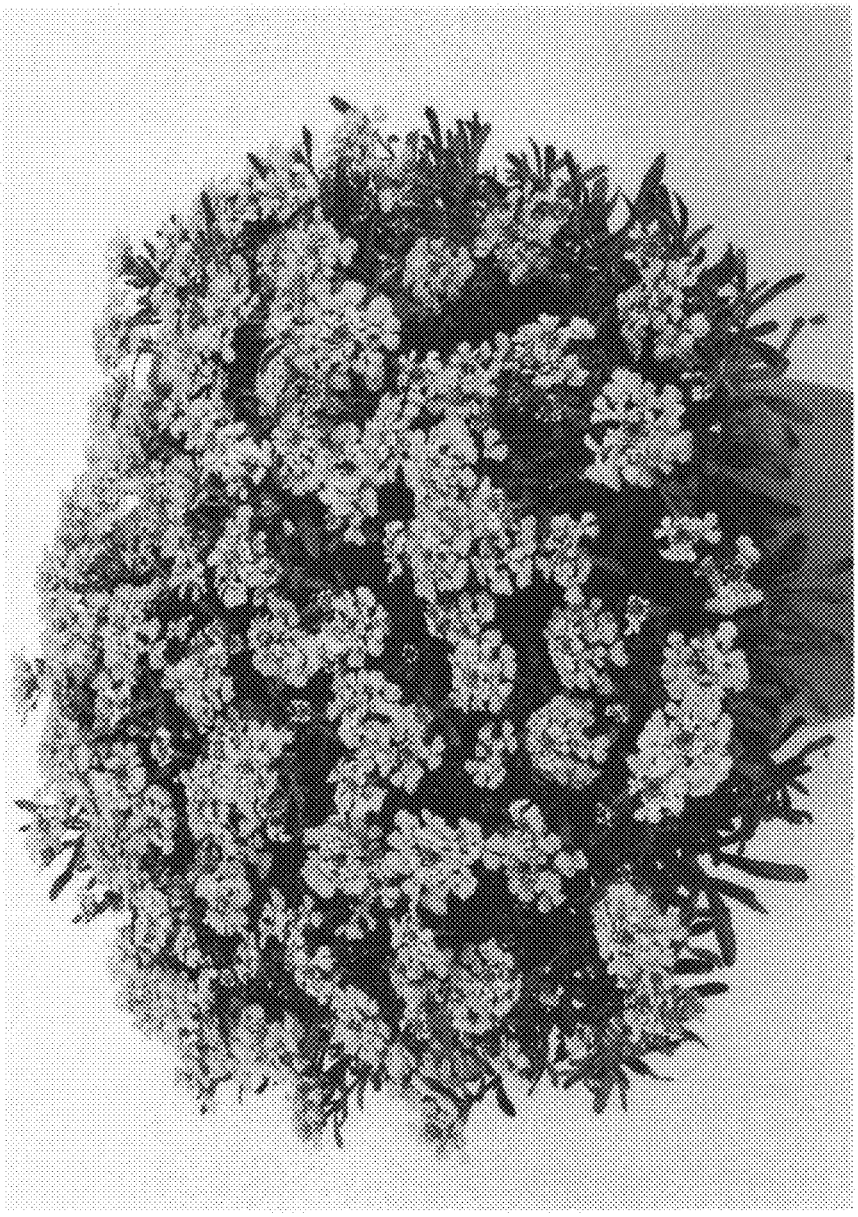

Latin name of the genus and species: *Iberis sempervirens*.
Variety denomination: 'DIBFRFLAL'.

BACKGROUND OF THE INVENTION

The new *Iberis* cultivar is a product of a planned breeding program. The new variety was discovered as a seedling resulting from an open-pollination breeding program at a research greenhouse in Moshav Mishmar Hashiva, Israel during Spring of 2016. The interesting new variety was discovered during the Spring of 2017.

The seed parent is the unpatented, proprietary variety 'IB-13-260'. The pollen parent is unknown.

Asexual reproduction of the new cultivar has been performed by terminal vegetative cuttings. This was first performed at a research greenhouse in Moshav Mishmar Hashiva, Israel during the Spring of 2017 and has shown that the unique features of this cultivar are stable and reproduced true to type in more successive generations.

SUMMARY OF THE INVENTION

The cultivar 'DIBFRFLAL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DIBFRFLAL' These characteristics in combination distinguish 'DIBFRFLAL' as a new and distinct *Iberis* cultivar:

1. First year flowering.
2. Vernalization is not required for flowering.
3. Controlled plant growth with a mounded habit.
4. Light lavender flowers.

PARENTAL COMPARISON

Plants of the new cultivar 'DIBFRFLAL' are are similar to the seed parent in most horticultural characteristics. The new variety 'DIBFRFLAL' differs in the following:

1. The new variety flowers earlier than the seed parent.
2. The hew variety has a more compact plant habit.
3. The new variety has a mounded plant habit; the seed parent has a spreading plant habit.

COMMERCIAL COMPARISON

Plants of the new cultivar 'DIBFRFLAL' are comparable to the unpatented commercial variety *Iberis* 'Snowsurfer'. The two *Iberis* varieties are similar in most horticultural characteristics; however, the new variety 'DIBFRFLAL' differs in the following:

1. Plants of the new variety are not observed to produce seeds; plants of this comparator are observed to produce seeds, which should result in a shorter life span.
2. The new variety has a mounded plant habit; this comparator has an upright plant habit.
3. Flowers of the new variety are light lavender; flowers of this comparator are white.

Plants of the new cultivar 'DIBFRFLAL' can also be compared to the unpatented commercial variety *Iberis* 'Snow Cushion'. The two *Iberis* varieties are similar in most horticultural characteristics; however, the new variety 'DIBFRFLAL' differs in the following:

1. Plants of the new variety flower earlier than plants of this comparator.
2. Plants of the new variety are dense and mounding; plants of this comparator are less dense and flattened, trailing.
3. Flowers of the new variety are light lavender; flowers of this comparator are white.

BRIEF DESCRIPTION OF THE PHOTOGRAPHS

The accompanying photograph in FIG. 1 illustrates in full color a typical flowering plant of 'DIBFRFLAL' in a 20 cm pot at approximately 20 weeks from a rooted cutting.

Figure 2:
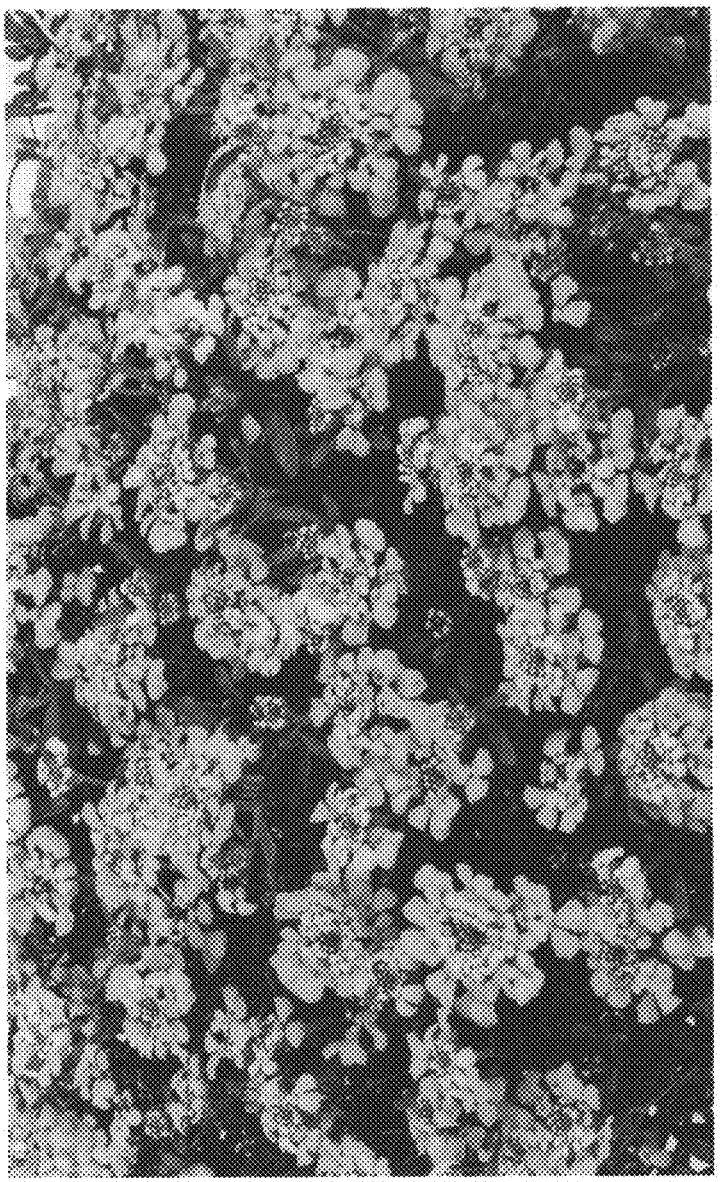

FIG. 2 illustrates a close up of flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'DIBFRFLAL' plants grown outdoors in Mishmar Hashiva, Israel. The growing temperature ranged from approximately 10° C. to 28° C. during the day and from approximately 6° C. to 18° C. during the night. General light conditions are normal sunlight and numerical values represent averages of typical plant types.

Botanical classification: *Iberis sempervirens* 'DIBFRFLAL'.

PROPAGATION

Type of propagation typically used: Vegetative terminal cuttings.

Time to initiate roots: About 7 to 14 days at approximately 24° C.

Time to produce a rooted cutting or liner: About 14-21 days at approximately 24° C.

PLANT

Type: Flowering perennial.

Age of plant described: Approximately 13 weeks from a rooted cutting.

Overall plant growth habit: Mounded.

Height: Approximately 25 cm.

Plant spread: Approximately 30 cm.

Growth rate: Moderate to rapid.

Characteristics of main stems:

*Length.*—Approximately 8-12 cm.

*Diameter.*—Approximately 0.3 cm.

*Color.*—Young Stems Close to RHS Yellow-Green 144A. Mature stems near Green 143C.

Moderate anthocyanin at nodes near Purple N77A.

*Texture.*—Glabrous.

*Strength.*—Flexible.

*Internode.*—Approximately 0.5 cm.

*Quantity per plant.*—Approximately 200.

Root description: Fibrous, color white to cream, not accurately measured with RHS chart.

Rhizomes: Not observed.

FOLIAGE

Leaf:

*Arrangement.*—Simple, alternate or spiraled.

*Average length.*—Approximately 3.8 cm.

*Average width.*—Approximately 3 to 5 mm.

*Shape of blade.*—Linear.

*Apex.*—Rounded.

*Base.*—Truncate.

*Attachment.*—Sessile.

*Margin.*—Entire.

*Texture of top surface.*—Glabrous.

*Texture of bottom surface.*—Glabrous.

*Appearance of top surface.*—Matte.

*Appearance of bottom surface.*—Matte.

*Leaf internode length.*—Approximately 4 to 6 mm.

*Leaves per main branch.*—Average range 16 to 22.

*Color.*—Young foliage upper side: Near RHS Green 137C. Young foliage under side: Near RHS Green 137C. Mature foliage upper side: Near RHS Green N137B. Mature foliage under side: Near RHS Green 137B.

*Venation.*—Type: Pinnate. Venation color upper side: Near RHS Green 137D. Venation color under side: Near RHS Green 139C.

FLOWER

Natural flowering season: Spring through Summer.

Inflorescence type and habit: Domed corymb.

Inflorescences per plant: Average range 100 to 180.

Quantity of flowers: About 20 to 30 open flowers and 20 and 25 buds per inflorescence.

Inflorescence size:

*Height.*—Approximately 3.0 o 3.5 cm.

*Diameter.*—Approximately 4.0 cm.

Individual flowers:

Size:

*Diameter.*—Approximately 5 mm.

*Depth.*—Approximately 3 mm to 4 mm.

*Persistence.*—Self-cleaning.

*Fragrance.*—Light.

Petals:

*Length of petal.*—Approximately 3 mm to 10 mm.

*Width of petal.*—Approximately 3 mm to 7 mm.

*Apex.*—Broad rounded.

*Base.*—Tapered.

*Shape of petal.*—Spatulate.

*Petal margin.*—Entire.

*Petal number.*—4.

*Petal texture.*—Glabrous all surfaces.

Color:

*Upper surface at first opening.*—Near RHS Purple 76D.

*Upper surface at maturity.*—Near RHS Purple 76A.

*Upper surface at fading.*—Near RHS Purple 76D.

*Under surface at first opening.*—Near RHS White N155BB.

*Under surface at maturity.*—Near RHS Purple 76C.

*Under surface at fading.*—Near RHS Purple 76D.

Bud:

*Shape.*—Orbicular.

*Length.*—Approximately 2 mm.

*Diameter.*—Approximately 2.5 mm.

*Color.*—Near Purple 75D.

Peduncle:

*Length.*—Approximately 2 cm.

*Diameter.*—Approximately 2 mm.

*Texture.*—Glabrous.

*Color.*—Near Green 137B.

*Orientation.*—Upright.

*Strength.*—Moderate, flexible.

Pedicel:

*Length.*—2 to 3 mm.

*Diameter.*—1 mm.

*Texture.*—Glabrous.

*Color.*—Near Green 137B.

*Angle.*—Average angle 30°.

*Strength.*—Moderate.

Sepal:

*Quantity.*—4.

*Length.*—2 mm.

*Width.*—2 mm.

*Texture.*—Glabrous all surfaces.

*Color.*—Upper surface: Near Green 143B. Lower surface Near Green 143C.

*Apex.*—Acute.

*Margin.*—Entire.

REPRODUCTIVE ORGANS

Androecium:

Anthers:

*Shape.*—Ovoid.

*Length.*—Approximately 0.2 mm.

*Color.*—Near Purple 76D.

*Pollen.*—Not observed.

*Stamen Quantity.*—6.

Gynoecium:

Pistil:

*Number.*—1.

*Length.*—Approximately 0.5 mm.

*Style.*—Length: Approximately 0.3 mm. Color: White 155A.

*Stigma.*—Shape: Linear. Color: White 155A. Ovary Color: Yellow-Green 149C.

OTHER CHARACTERISTICS

Fruits and seeds: Not observed to date.

Disease/pest resistance: Neither resistance nor susceptibility to normal diseases of *Iberis sempervirens* observed.

Temperature tolerance: Low temperature tolerance not observed, typically *Iberis sempervirens* tolerate temperatures in USDA zones 3-9.

What is claimed is:

1. A new and distinct cultivar of *Iberis* plant named 'DIBFRFLAL' as herein illustrated and described.

* * * * *